(12) United States Patent  
Liang et al.

(10) Patent No.: US 10,215,709 B2
(45) Date of Patent: Feb. 26, 2019

(54) DETECTING SYSTEM

(71) Applicants: BOE TECHNOLOGY GROUP CO., LTD., Beijing (CN); BEIJING BOE DISPLAY TECHNOLOGY CO., LTD., Beijing (CN)

(72) Inventors: Kui Liang, Beijing (CN); Jianfeng Yuan, Beijing (CN); Seung Moo Rim, Beijing (CN)

(73) Assignees: BOE TECHNOLOGY GROUP CO., LTD., Beijing (CN); BEIJING BOE DISPLAY TECHNOLOGY CO., LTD., Beijing (CN)

( * ) Notice: Subject to any disclaimer, the term of this patent is extended or adjusted under 35 U.S.C. 154(b) by 973 days.

(21) Appl. No.: 14/375,630

(22) PCT Filed: Nov. 12, 2013

(86) PCT No.: PCT/CN2013/086979
§ 371 (c)(1),
(2) Date: Jul. 30, 2014

(87) PCT Pub. No.: WO2015/014041
PCT Pub. Date: Feb. 5, 2015

(65) Prior Publication Data
US 2016/0266048 A1 Sep. 15, 2016

(30) Foreign Application Priority Data
Jul. 31, 2013 (CN) .......................... 2013 1 0328461

(51) Int. Cl.
*G01N 21/95* (2006.01)
*G01N 21/88* (2006.01)
(Continued)

(52) U.S. Cl.
CPC ......... *G01N 21/95* (2013.01); *G01N 21/8806* (2013.01); *G01N 21/956* (2013.01);
(Continued)

(58) Field of Classification Search
CPC .............................................. G01N 2021/9513
See application file for complete search history.

(56) References Cited

U.S. PATENT DOCUMENTS 4,541,723 A * 9/1985 Pirlet .................. G01B 11/245
356/3.02
4,943,732 A 7/1990 Economou
(Continued)

FOREIGN PATENT DOCUMENTS

CN 1996441 A 7/2007
CN 101210886 A 7/2008

OTHER PUBLICATIONS

Second Chinese Office Action Appln. No. 201310328461.7; dated Sep. 28, 2015.
(Continued)

*Primary Examiner* — Hina F Ayub
*Assistant Examiner* — Amanda Merlino
(74) *Attorney, Agent, or Firm* — Ladas & Parry LLP

(57) ABSTRACT

A detecting system configured for detecting flaws on an object to be detected, increasing: a display processing device; an tunable light source; at least one light transmitter, wherein the tunable light source is connected with the at least one light transmitter; at least one light receiver configured for cooperating with the at least one light transmitter, wherein the at least one light receiver is connected with the display processing device; wherein the display processing device is connected to the tunable light source, receives and processes information provided by the light receiver to form detection images, and is operable to adjust the tunable light source.

17 Claims, 1 Drawing Sheet

(51) Int. Cl.
*G01N 21/956* (2006.01)
*G02F 1/13* (2006.01)

(52) U.S. Cl.
CPC ............... *G01N 2021/8835* (2013.01); *G01N 2021/9513* (2013.01); *G01N 2201/062* (2013.01); *G01N 2201/12* (2013.01); *G02F 1/1309* (2013.01)

(56) References Cited

U.S. PATENT DOCUMENTS

| | | | | |
|---|---|---|---|---|
| 6,221,544 | B1* | 4/2001 | Hayashi | ............... G01N 21/59 347/107 |
| 7,714,996 | B2* | 5/2010 | Yan | ............... G01N 21/8901 356/237.1 |
| 2003/0184741 | A1 | 10/2003 | Ueta | |
| 2004/0201838 | A1* | 10/2004 | Lee | ............... G01N 21/956 356/237.2 |
| 2014/0185040 | A1* | 7/2014 | Lin | ............... G01N 21/958 356/239.1 |

OTHER PUBLICATIONS

International Preliminary Report on Patentability dated Feb. 2, 2016; PCT/CN2013/086979.

First Chinese Office Action Appln. No. 201310328461.7; dated May 26, 2015.

International Search Report Appln. No. PCT/CN2013-086979; dated Apr. 2, 2014.

* cited by examiner

DETECTING SYSTEM

TECHNICAL FIELD

Embodiments of the present invention relate to a detecting system.

BACKGROUND

The liquid crystal panel in a liquid crystal display plays a key role responsible for the display effect of the liquid crystal display such as brightness, contrast, colorfulness, etc. A traditional liquid crystal panel comprises an array substrate and a color filter substrate disposed opposite to each other with a liquid crystal layer being sandwiched therebetween.

In the actual manufacturing process of liquid crystal panels, due to the influence of production processes, phenomena such as flaws tend to occur in the manufactured liquid crystal panels, which will influence use of the liquid crystal panels. With the mass production of liquid crystal panels, various linear mura flaws or flaky mura flaws will occur on array substrates and/or color filter substrates due to various reasons in the production processes, which will impose adverse impacts on the display effect of the liquid crystal panels. Therefore, it is desired to detect mura flaws to improve product yields, and to improve processes with feedbacks to the production line.

In traditional manufacturing processes, the detection on mura flaws generated in the production process of liquid crystal panels is generally accomplished by technicians with the help of sodium lamp or mercury lamp. This approach can detect obvious and prominent mura defects in liquid crystal panels. However, since mura flaws on some types of liquid crystal panels are too weak to be recognized by naked eyes, it is impossible to define boundaries of mura flaws and use of the above-mentioned traditional approach will introduce difficulties for detection, which makes it unable to conduct detail and in-depth analysis in-time and improve product process, hence reducing product yields and bringing about wastes.

SUMMARY

Embodiments of the present invention provide a detecting system that can address problems of low yields and wastes for liquid crystal panel products in traditional technology.

One aspect of the present invention provides a detecting system configured for detecting flaws on an object to be detected, comprising: a display processing device; an tunable light source; at least one light transmitter, wherein the tunable light source is connected with the at least one light transmitter; at least one light receiver configured for cooperating with the at least one light transmitter, wherein the at least one light receiver is connected with the display processing device; wherein the display processing device is connected to the tunable light source, receives and processes information provided by the light receiver to form detection images, and is operable to adjust the tunable light source.

In order to save space costs, for example, the number of light receivers and the number of light transmitters may be equal to each other; for example, the light receivers and the light transmitters may be fixed together in a combination manner to form light transceivers.

For example, the detecting system may further comprise a carrying platform; for example, the light transceivers and the carrying platform may be connected via a support.

In order to obtain a clear and complete flaw image, for example, the light transceivers may comprise a first light transceiver, a second light transceiver and a third light transceiver; the first light transceiver comprises a first light transmitter and a first light receiver fixed together in a combination manner; the second light transceiver comprises a second light transmitter and a second light receiver fixed together in a combination manner; and the third light transceiver comprises a third light transmitter and a third light receiver fixed together in a combination manner; light emitted from the first light transmitter is perpendicular to the carrying platform, and the first light receiver receives first reflected light of the light emitted from the first light transmitter; an angle between light emitted from the second light transmitter and the carrying platform is adjustable and of an acute angle, and the third light receiver receives second reflected light of the light emitted from the second light transmitter; an angle between light emitted from the third light transmitter and the carrying platform is adjustable and of an acute angle, and the second light receiver receives third reflected light of the light emitted from the third light transmitter.

For better detection, for example, spatial positions of the first light transceiver, the second light transceiver and the third light transceiver are all adjustable by a translational stepping manner in a horizontal direction and an elevation direction. For example, the stepping regulation may have a precision of 0.001 millimeter.

For example, in this detecting system, the carrying platform can be adjusted by a translation and/or overturning manner.

In order to facilitate detecting flaws of different types on different objects to be detected, for example, the tunable light source may comprise light of a plurality of different types and adjustable intensities.

For example, the display processing device may comprise a computer and a data collecting and processing unit connected with the computer; both the tunable light source and the light receiver are connected with the data collecting and processing unit.

In order to facilitate analyzing flaws after detection, for example, the detecting system may further comprise a probe, wherein the probe is fixed on the carrying platform and electrically connected with the computer; and the probe is configured to mark or cut flaws of the object to be detected placed on the carrying platform.

For example, the object to be detected may be a liquid crystal panel, and the flaws are mura on the liquid crystal panel.

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

DETAILED DESCRIPTION

In order to make objects, technical details and advantages of the embodiments of the invention apparent, the technical solutions of the embodiments will be described in a clearly and fully understandable way in connection with the drawings related to the embodiments of the invention. Apparently, the described embodiments are just a part but not all of the embodiments of the invention. Based on the described embodiments herein, those skilled in the art can obtain other embodiment(s), without any inventive work, which should be within the scope of the invention.

Figure 1:
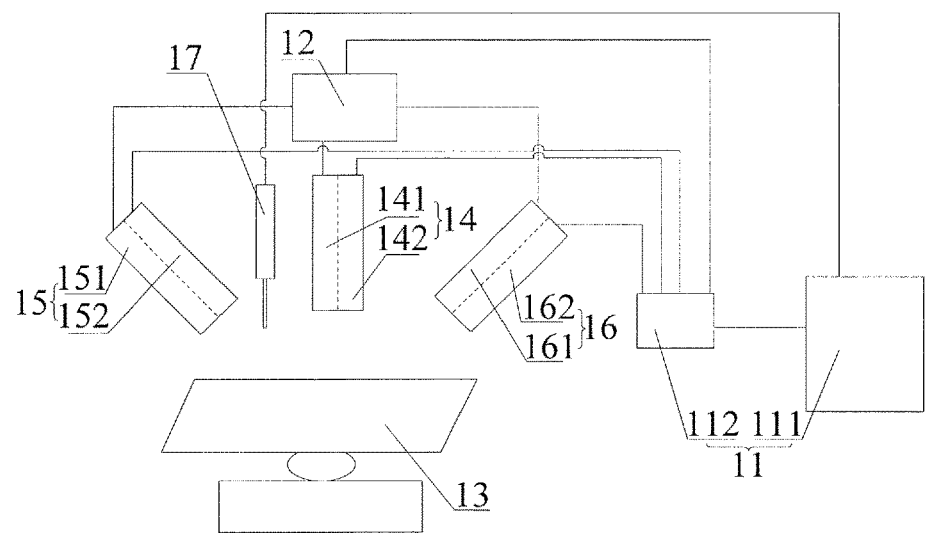
FIG. 1 is a structure diagram of a detecting system provided in an embodiment of the present invention.

An embodiment of the present invention provides a detecting system configured for detecting flaws on an object to be detected. As illustrated in FIG. 1, the detecting system comprises: a display processing device 11, a tunable light source 12, at least one light transmitter and at least one light receiver. The display processing device 11 is connected to the tunable light source 12; the tunable light source 12 is connected to the at least one light transmitter; and the at least one light receiver cooperates with the at least one light transmitter and is connected to the display processing device 11; and the display processing device 11 is configured to receive and process information provided by the light receiver and form a detection image, and adjusts the tunable light source 12.

In the detecting system provided in the embodiments of the present invention, the display processing device is provided, and can be connected with the tunable light source and can control ON, OFF and regulation of the tunable light source. The tunable light source is connected with the light transmitter such that the light of the tunable light source can be emitted outward by the light transmitter to illuminate the object to be detected (such as a liquid crystal panel) on a carrying platform and be reflected, and the reflected light is received by the light receiver and fed back into the display processing device connected with the light receiver for automatic image formation. Thereby, by adjusting the intensity and wavelength of the light in the tunable light source and by the cooperation between the light transmitter and the light receiver, as well as by the control of the display processing device, it is possible to form images automatically in the display processing device, which avoids invisibility for naked eyes in manual observation and enables operators to detect flaws on liquid crystal panels effectively and conveniently, and in turn to make improvements in the production processes, improve product yields and save costs.

It is to be noted here that the above-mentioned display processing device may be a device formed by integrating a display and a control processor, which may be an integral device or a device formed by connecting a plurality of relevant parts. The tunable light source may also be an independent adjustable light source, then it may be not connected with the display processing device, and operations such as on, off and regulation of the light source can be accomplished by an embedded self-control program or manual control. The light of the tunable light source is emitted via the light transmitter. The tunable light source and the light transmitter may be connected by an optical fiber to increase light utilization.

One example of the tunable light source comprises a white light emitting diode (LED), as the light source, and a light filter or a grating, and it is possible to tune the wavelength and intensity of emitted light by modifying the light filter or the grating. Another example of the tunable light source comprises a plurality sets of illuminators (for example LEDs), and each illuminator has different light emission wavelength and tunable intensity. The light transmitter may comprise an embedded optical amplifier, for example, to convert non-linear light into linear light such that the light intensity of the emitted light is obtained by the photometer. The light receiver is for example a light collecting device, which may comprise charge coupling device (CCD) image sensors to convert received optical signals into digital signals and for example transmit these digital signals to a computer to display images for an operator to process. The light receiver may further comprise a photometer for detecting light intensity and feeding back detection results to the display processing device.

In addition, in order to detect flaws on flat objects to be detected such as liquid crystal panels, those skilled in the art can readily use the above-mentioned parts to form a set of liquid crystal panel flaw automatic detecting system according to the teachings of embodiments of the present invention, and this system can have improved identification effect and efficiency as compared with the traditional visual inspection by technicians with the help of lamp light. The present embodiment is described with detecting flaws on liquid crystal panels, namely mura flaws as an example.

In the embodiment illustrated in FIG. 1, the number of light receivers and the number of light transmitters may be equal to each other. For example, the light receiver and the light transmitter are fixed together in combination to constitute a light transceiver. For example, the light transceiver and the carrying platform 13 are connected by a support (not illustrated in FIG. 1). In detecting flaws on liquid crystal panels with the above-mentioned parts, the operators can detect flaws by holding a light transmitter and a light receiver. Of course, in order to save manual works, it is also possible to automatically detect flaws by controlling positions and operations of the light transceiver with the display processing device 11. While in manual operation, due to the poor stability of the light transmitter and light receiver that are handheld, errors tend to occur in detection, which makes image formation of the processing device inaccurate. Therefore, it is desirable to provide a support to realize stable fixture of the light transmitter and light receiver, and such type of fixture mode is equally applicable to automatic control detection.

In order to save space costs more, and at the same time to guarantee the entire appearance design quality of the detecting system, it is possible to fix the light transmitter and the light receiver together in a combination manner to constitute a light transceiver without influencing the detection effect. Fixing the light transmitter and the light receiver together in a combination manner may be realized by providing the light transmitter and the light receiver that are integrated while producing or by fixing a separate light transmitter and a separate light receiver together in a manner. Thereafter, the light transceiver is fixed and connected with the carrying platform 13 via a support; of course it may be fixed onto another object, such as a separately provided supporting table, a supporting frame etc.

For example, in detecting flaws on a liquid crystal panel, in order to further improve detection accuracy, it is possible to implement fully automated control. Now, the tunable light source may be automatically controlled through the display processing device and the optical channel between the tunable light source and the light transceiver may also be controlled. The light transceiver may be automatically controlled in a manner similar to a mechanical arm, that is, a controller may be further provided on the support to automatically adjust the spatial position and the angle of the light transceiver as required. The light source may be a fluorescent lamp or a light emitting diode.

While practically using the system for detection, as illustrated in FIG. 1, the light transceiver may comprise a first light transceiver 14, a second light transceiver 15 and a third light transceiver 16 for improving detection efficiency. These three light transceivers are all located above the platform 13. The first light transceiver 14 comprises a first light transmitter 141 and a first light receiver 142 fixed together in a combination manner; the second light transceiver 15 comprises a second light transmitter 151 and a second light receiver 152 fixed together in a combination manner; and the third light transceiver 16 comprises a third light transmitter 161 and a third light receiver 162 fixed together in a combination manner. According to the detection theory and experience, when a liquid crystal panel is placed on the carrying platform 13 horizontally, by emitting light from right above it and receiving reflected light in the elevation direction, a basic planar morphology of the flaws on the liquid crystal panel can be obtained, and in this case it is also possible to only use the first light transceiver 14, and the first light transmitter 141 in the first light transceiver 14 emits light perpendicularly to the liquid crystal panel and the first light receiver 142 receives first reflected light of the light emitted from the first light transmitter 141. Please note that the above-mentioned "perpendicularly" does not mean the case of being absolute perpendicular, and an error within 1-5 degrees may be negligible and the respective direction can be hence defined as a vertical direction.

In the above-mentioned process, the spatial position in the horizontal direction and vertical direction of the first light transceiver 14 may be changed by manually operating or automatically controlling, and in order to guarantee the detection precision, its regulation may be translational stepping regulation, and the precision of stepping regulation may be for example 0.001 mm to guarantee detection accuracy. In addition, in this process, for example, when a flaw region is detected (that is, when the reflected light changes), the display processing device 11 forms an images of it. Then, the display processing device 11 can send control instructions to the tunable light source, according to preset settings, to automatically analyze the definition of images so as to change its wavelength and light intensity, and therefore a clear planar morphology of flaws is obtained. Finally, a positioning device on the first light transceiver 14 may be used for realizing positioning and for facilitating subsequent operations such as marking.

It should be noted that the first light transceiver 14 may be subjected to minute angle regulation if its error angle allows, that is, adjusting the angle between the light emitted from the first light transmitter 141 and the liquid crystal panel.

With respect to the planar flaw morphology obtained by the first light transceiver 14, in analyzation upon it, since the morphology is obtained in one direction only, the integrity thereof is poor and the reference analysis value is not high. Particularly to a flaw with solid shape, the accuracy is not high. In this way, a second light transceiver 15 and a third light transceiver 16 can be added. The angle between the light emitted from the second light transmitter 151 of the second light transceiver 15 and the liquid crystal panel is adjustable and of an acute angle, the third light receiver 162 in the third light transceiver 16 receives second reflected light of light emitted from the second light transmitter 151; the angle between the light emitted from the third light transmitter 161 of the third light transceiver 16 and the liquid crystal panel is adjustable and of an acute angle, the second light receiver 152 in the second light transceiver 15 receives third reflected light of light emitted from the third light transmitter 161.

In the structure illustrated in FIG. 1, after obtaining the basic planar morphology image of flaws via the first light transceiver 14, the controller closes the optical channel between the tunable light source 12 and the first light transmitter 141 and opens the optical channel between the tunable light source 12 and the second light transmitter 151 and the third light transmitter 161. Then according to the light reflection law, the second light transmitter 151 and the third light receiver 162 are matched with each other, and the third light transmitter 161 and the second light receiver 152 are matched with each other. In practical operations, it is possible to adjust the spatial positions of the second light transceiver 15 and the third light transceiver 16 in the horizontal direction and the elevation direction also with a translational stepping regulation approach. At the same time, it is also possible to change the angle between the light emitted from the second light transceiver 15 and the third light transceiver 16 and the liquid crystal panel, the wavelength and light intensity of the tunable light source by manual control or automatic control, so as to obtain a clear and complete image in the display processing device 11. In this case, the resulting image may be a planar structure, or may be a three-dimensional structure depending on the characteristics of flaws on the liquid crystal panel.

It is to be noted here that the adjustment of the angle between the light emitted from the second light transceiver 15 and the third light transceiver 16 and the liquid crystal panel may be an overall angle change, that is, the adjustment of light transceiver causes corresponding adjustment of emitted light; and also possibly internal structure of the light transceiver is changed to control the direction of emitted light. Furthermore, in order to further reduce detection error, it is possible to add one or more light transceivers to realize better detection effect.

When a flaw is detected on the liquid crystal panel, in order to more quickly obtain a clear image, and when the light transceiver is not easy to adjust, it is possible to manually or automatically control the carrying platform 13 to control its horizontal and/or overturn adjustment, hence obtaining a preferred detection position. In detecting flaws on a liquid crystal panel, in the light reflection process, the liquid crystal panel as a reflection plane may be immobilized, may also move separately along with the platform 13 or move together with the light transceiver, so as to accelerate the detection of flaws and the determination on the optimal detection position to improve detection efficiency. In adjusting the carrying platform 13, it is mainly for the detection process using the second light transceiver 15 and the third light transceiver 16, while when obtaining the basic planar flaw morphology with the first light transceiver 14, the carrying platform 13 may not be adjusted, which has little influence on the detection results.

In the detecting system described in the above-mentioned embodiments, the tunable light source 12 may comprise light of different types (wavelengths) and adjustable intensity. In the traditional technology, generally one type of light is used to accomplish detection. However different liquid crystal panels have different flaws, and have different light induction capabilities. Therefore, a tunable light source comprising a plurality of different types is provided to detect different types of flaws on liquid crystal panels. For example, the tunable light source may comprise white light, red light, green light, blue light and yellow light each of different wavelength, and therefore has a broader application range and better practicability. In addition, the light intensity is generally adjustable in use mainly for the purpose of obtaining an image of high definition.

For the type conversion (wavelength change) between different types of light and the control on light intensity, they may be accomplished by automatic or manual control in the tunable light source or by automatic or manual control in the display processing device.

In addition, in one example, as illustrated in FIG. 1, the display processing device 11 may comprise a computer 111 and a data collecting and processing unit 112 connected with the computer 111; both the tunable light source 12 and the light receiver (light receiver 142, 152, 162) are connected with the data collecting and processing unit 112. For the specific operation process of imaging by means of light reflection, it is accomplished with the help of particular modules such as the optical sensor, the image inversion unit. Therefore, it is possible to form the display processing device 11 by assembling the data collecting and processing unit 112 and the computer 111 together, in which the computer 111 is configured to receive data and form images, and control the regulation of tunable light source and parts at the same time, and the data collecting and processing unit 112 is configured to analyze the obtained data in connection with the reflected light to convert them into specific images and display the images in the computer 111. The control instructions of the computer 111 may be executed directly by the data collecting and processing unit 112, which avoids the provision of signal converting devices etc. in the computer 111 and saves costs. The computer 111 may be a dedicated or general purpose computing device, and the data collecting and processing unit 112 may be implemented in a manner known in the art. Here, the computer 111 and the data collecting and processing unit 112 may be implemented in hardware, software, and firmware or any combination thereof.

After flaws on the liquid crystal panel are detected, they need to be analyzed to find out specific causes of them and produce feedbacks to the production line for process improvements, hence improving product yields. To facilitate analysis, in one example as illustrated in FIG. 1, a probe 17 may be added to be connected with the computer 111 for marking or cutting flaws on the liquid crystal panel. As described in the above-mentioned embodiments, a positioning device may be provided on the first light transceiver 14. Marking or cutting by the probe 17 may be well controlled by the positioning of the positioning device. The marking or cutting operation of the probe 17 may be manually controlled, in which case the probe 17 may be connected with the carrying platform 13 for realizing stable fixture and operation. For automatic controlling by a computer, a structure similar to a mechanical arm is needed to control the marking or cutting operation.

A liquid crystal panel typically has a large surface area while flaws are small in area, which is not helpful for further marking, cutting or analyzing well after detection. Therefore, the flaw images obtained by the computer 111 may be magnified, or an image magnifying device may be added on the support of the carrying platform 13 to facilitate better marking or cutting by the probe and further analyzing the images.

In the detecting system described in the above-mentioned embodiments, the object to be detected on the carrying platform 13 may be a liquid crystal panel, or a tabular object to be detected of other types or in the industry. When it is a liquid crystal panel, the flaws on it are for example mura flaws.

Figure 2:
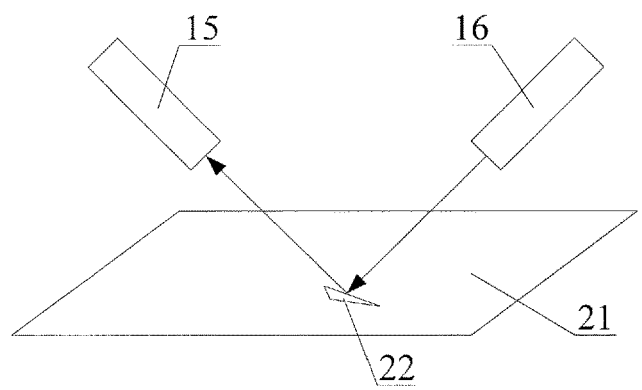
FIG. 2 is a simple schematic diagram at a moment when a second light transceiver and a third light transceiver in FIG. 1 cooperate to detect.
Figure 3:
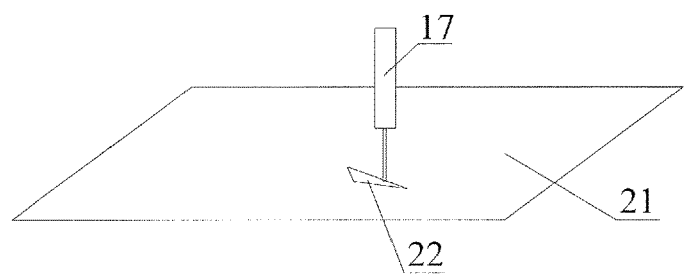
FIG. 3 is a simple schematic diagram at a moment when a probe in FIG. 1 is marking or cutting a flaw detected in an object to be detected.

The working process of the detecting system described in the above-mentioned embodiments will be illustrated in detail below with reference to FIGS. 1 to 3. FIGS. 2 and 3 contain a liquid crystal panel 21 and flaws 22 on the liquid crystal panel 21.

First of all, the liquid crystal panel 21 is placed horizontally on the carrying platform 13 and stably fixed in place to prevent the liquid crystal panel 21 from displacing or dropping when the carrying platform 13 needs to be adjusted. Then the tunable light source 12 and the optical channel between the tunable light source and the first light transceiver 14 are turned on under the control of the computer 111, and the first light transceiver 14 is regulated by translational stepping in the horizontal direction and the elevation direction under the control of the computer 111, to determine positions of the flaws of the liquid crystal panel and reflected light is processed by the data collecting and processing unit 112 to form images in the computer 111. Then, the computer controls the change of wavelength and intensity of light in the tunable light source by means of image definition, so as to obtain a clear planar morphology image of flaws.

Then, the optical channel between the first light transceiver 14 and the tunable light source 12 is closed under the control of the computer 111 to prevent interference, and at the same time the optical channel between the tunable light source 12 and the second light transceiver 15 and the third light transceiver 16 is opened to allow the second and third light transceivers (15,16) to cooperate to implement specific detection of the flaws on the liquid crystal panel and obtain a complete, accurate and clear flaw image in the computer 111. In this process, it is required to automatically control and regulate the positions of the second light transceiver 15, the third light transceiver 16 and the direction of respective emitted light according to the definition and integrity of flaw images in the computer 111. It is also possible to adjust the position and angle of the carrying platform 13 at the same time as required.

Finally, to facilitate analysis, the detected flaws are marked or cut by the probe 17 under the control of the computer 111 to facilitate further analysis, and thereby improving production process.

It is to be noted here that FIGS. 2 and 3 are simple schematic diagrams for only showing specific operations at one moment in detection. In specific operation, the specific flaw morphology may be obtained through a plurality of detections, marking or cutting with multiple angles.

Terms "first", "second" etc. are only used for the purpose of description, and can not be interpreted as indicating or implying relative importance or implicitly indicating the number of stated technical features. Thereby, features defined by "first", "second" etc. may explicitly or implicitly comprise one or more of the features.

In the description of the present invention, it is to be noted that unless otherwise stated and defined, terms "mount", "connected with" and "connected" should be interpreted broadly. For example, it may be a fixed connection, or a detachable connection, or an integral connection; it may be a direct connection, or an indirect connection via an intermediate media, or inside communication of two elements. For those of ordinary skill in the art, specific meanings of the above-mentioned terms in the present utility model may be understood depending on specific circumstances.

What are described above is related to the illustrative embodiments of the disclosure only and not limitative to the scope of the disclosure; the scopes of the disclosure are defined by the accompanying claims.

The invention claimed is:

1. A detecting system configured for detecting flaws on an object to be detected, comprising:
   a display processing device;
   a tunable light source;
   at least one transceiver, comprising a light transmitter and a light receiver, wherein the tunable light source is connected with the light transmitter, and the light receiver and the light transmitter are fixed together in a combination manner and contact directly with each other, and the light receiver configured for cooperating with the light transmitter, wherein the receiver is connected with the display processing device;
   wherein the display processing device is connected to the tunable light source, and is configured to receive and process information provided by the light receiver to form detection images, and is operable to adjust the tunable light source.

2. The detecting system of claim 1, wherein a number of light receivers and a number of light transmitters are equal to each other, and the light receiver and the light transmitter are fixed together in a combination manner to form a light transceiver.

3. The detecting system of claim 2, further comprising a carrying platform, wherein the light transceiver and the carrying platform are connected via a support.

4. The detecting system of claim 2, wherein the light transceivers comprises a first light transceiver, a second light transceiver and a third light transceiver; the first light transceiver comprises a first light transmitter and a first light receiver fixed together in a combination manner; the second light transceiver comprises a second light transmitter and a second light receiver fixed together in a combination manner; and the third light transceiver comprises a third light transmitter and a third light receiver fixed together in a combination manner;
   light emitted from the first light transmitter is perpendicular to the carrying platform, and the first light receiver receives first reflected light of the light emitted from the first light transmitter;
   an angle between light emitted from the second light transmitter and the carrying platform is adjustable and of an acute angle, and the third light receiver receives second reflected light of the light emitted from the second light transmitter; and
   an angle between light emitted from the third light transmitter and the carrying platform is adjustable and of an acute angle, and the second light receiver receives third reflected light of the light emitted from the third light transmitter.

5. The detecting system of claim 4, wherein spatial positions of the first light transceiver, the second light transceiver and the third light transceiver are all adjustable by a translational stepping manner in a horizontal direction and an elevation direction.

6. The detecting system of claim 2, wherein the display processing device comprises a computer and a control processor connected with the computer;
   both the tunable light source and the light receiver are connected with the control processor.

7. The detecting system of claim 6, further comprising a probe, wherein the probe is fixed on the carrying platform and electrically connected with the computer; and the probe is configured to mark or cut flaws of the object to be detected placed on the carrying platform.

8. The detecting system of claim 1, further comprising a carrying platform, wherein the at least one transceiver and the carrying platform are connected via a support.

9. The detecting system of claim 8, wherein the carrying platform can be adjusted by a translation and/or overturning manner.

10. The detecting system of claim 1, wherein the at least one transceiver comprises a first light transceiver, a second light transceiver and a third light transceiver; the first light transceiver comprises a first light transmitter and a first light receiver fixed together in a combination manner; the second light transceiver comprises a second light transmitter and a second light receiver fixed together in a combination manner; and the third light transceiver comprises a third light transmitter and a third light receiver fixed together in a combination manner;
    light emitted from the first light transmitter is perpendicular to the carrying platform, and the first light receiver receives first reflected light of the light emitted from the first light transmitter;
    an angle between light emitted from the second light transmitter and the carrying platform is adjustable and of an acute angle, and the third light receiver receives second reflected light of the light emitted from the second light transmitter; and
    an angle between light emitted from the third light transmitter and the carrying platform is adjustable and of an acute angle, and the second light receiver receives third reflected light of the light emitted from the third light transmitter.

11. The detecting system of claim 10, wherein spatial positions of the first light transceiver, the second light transceiver and the third light transceiver are all adjustable by a translational stepping manner in a horizontal direction and an elevation direction.

12. The detecting system of claim 10, wherein the carrying platform can be adjusted by a translation and/or overturning manner.

13. The detecting system of claim 1, wherein the tunable light source comprises light of a plurality of different types and adjustable intensities.

14. The detecting system of claim 1, wherein the display processing device comprises a computer and a control processor connected with the computer;
    both the tunable light source and the light receiver are connected with the control processor.

15. The detecting system of claim 14, further comprising a probe, wherein the probe is fixed on the carrying platform and electrically connected with the computer;
    and the probe is configured to mark or cut flaws of the object to be detected placed on the carrying platform.

16. The detecting system of claim 1, wherein the object to be detected is a liquid crystal panel, and the flaws are mura on the liquid crystal panel.

17. A detecting system configured for detecting flaws on an object to be detected, comprising:
    a display processing device;
    a tunable light source;
    a plurality of light transmitters, wherein the tunable light source is connected with at least one of the plurality of light transmitters;
    a plurality of light receivers configured for cooperating with the plurality of the light transmitters in one-to-one correspondence, wherein at least one of the plurality of light receivers is connected with the display processing device;

wherein the display processing device is connected to the tunable light source, and configured to receive and process information provided by the light receiver to form detection images, and is operable to adjust the tunable light source, the light receiver and the light transmitter are fixed together in a combination manner and contact directly with each other.

* * * * *